(12) United States Patent
Vogel et al.

(10) Patent No.: US 11,076,994 B2
(45) Date of Patent: Aug. 3, 2021

(54) APPARATUS FOR CHANGING THE REFRACTIVE POWER OF THE CORNEA

(71) Applicant: The General Hospital Corporation, Boston, MA (US)

(72) Inventors: Alfred Vogel, Luebeck (DE); Norbert Linz, Luebeck (DE); Sebastian Freidank, Luebeck (DE); Reginald Birngruber, Luebeck (DE)

(73) Assignee: The General Hospital Corporation, Boston, MA (US)

( * ) Notice: Subject to any disclaimer, the term of this patent is extended or adjusted under 35 U.S.C. 154(b) by 191 days.

(21) Appl. No.: 16/306,228

(22) PCT Filed: May 31, 2017

(86) PCT No.: PCT/US2017/035333
§ 371 (c)(1),
(2) Date: Nov. 30, 2018

(87) PCT Pub. No.: WO2017/210374
PCT Pub. Date: Dec. 7, 2017

(65) Prior Publication Data
US 2019/0209380 A1    Jul. 11, 2019

(30) Foreign Application Priority Data

May 31, 2016  (DE) .......................... 102016110005.6

(51) Int. Cl.
*A61F 9/013* (2006.01)
*A61F 9/00* (2006.01)
(Continued)

(52) U.S. Cl.
CPC .............. *A61F 9/013* (2013.01); *A61F 2/147* (2013.01); *A61F 2/148* (2013.01); *A61F 9/0017* (2013.01);
(Continued)

(58) Field of Classification Search
None
See application file for complete search history.

(56) References Cited

U.S. PATENT DOCUMENTS

| 4,298,004 A | 11/1981 | Schachar et al. |
| 5,215,104 A | 6/1993 | Steinert |

(Continued)

FOREIGN PATENT DOCUMENTS

| DE | 102007023293 | 9/2008 |
| FR | 2819722 | 7/2002 |

(Continued)

OTHER PUBLICATIONS

Extended European Search Report in Application No. 16808532.2, dated Jun. 15, 2018, 11 pages.

(Continued)

*Primary Examiner* — Leslie Lopez
(74) *Attorney, Agent, or Firm* — Fish & Richardson P.C.

(57) ABSTRACT

The invention relates to an apparatus for changing the refractive power of the cornea (1), in particular for correcting hyperopia or presbyopia, exhibiting injection means (13, 15) having at least one hollow needle (15) for injecting at least one optically transparent filling material having a predetermined refractive index into an intrastromal corneal pocket (7), characterized by a controllable injection drive (17) that is coupled at least indirectly to the injection means (13, 15) and is designed for changing an amount, to be injected, of the at least one filling material; a device for optical coherence tomography (OCT) (19) that is designed for monitoring the area of the corneal pocket (7) by means of measurement of depth profiles of the cornea (1) on a repeatedly cycled-through scan pattern; and a computing unit (21) that is designed and/or configured to determine from the measurement data of the OCT device (19) at least the radius of curvature of the front (3) of the cornea (1)

(Continued)

keeping pace temporally with the repetitions of the scan pattern cycle during the injection, wherein the computing unit (21) is designed and/or configured to control the injection drive (17) for changing the injected amount of the at least one filling material, and namely on the basis of the radius of curvature of the front (3) of the cornea (1) and/or such until a predetermined target criterion is fulfilled.

13 Claims, 2 Drawing Sheets

(51) Int. Cl.
*A61B 3/10* (2006.01)
*A61B 3/107* (2006.01)
*A61F 2/14* (2006.01)

(52) U.S. Cl.
CPC .............. *A61B 3/102* (2013.01); *A61B 3/107* (2013.01); *A61F 2240/002* (2013.01)

(56) References Cited

U.S. PATENT DOCUMENTS

| | | | |
|---|---|---|---|
| 5,306,500 | A | 4/1994 | Rhee et al. |
| 5,491,524 | A | 2/1996 | Hellmuth et al. |
| 5,565,519 | A | 10/1996 | Rhee et al. |
| 5,964,748 | A | 10/1999 | Peyman |
| 6,053,613 | A * | 4/2000 | Wei ............. A61B 3/1005 351/205 |
| 6,066,170 | A | 5/2000 | Lee |
| 6,485,413 | B1 * | 11/2002 | Boppart ......... A61B 1/00096 356/450 |
| 6,814,755 | B2 | 11/2004 | Lacombe et al. |
| 8,409,177 | B1 | 4/2013 | Lai |
| 2003/0014042 | A1 | 1/2003 | Juhasz et al. |
| 2004/0015234 | A1 | 1/2004 | Peyman |
| 2006/0216329 | A1 | 9/2006 | Peyman |
| 2008/0039825 | A1 | 2/2008 | Lai |
| 2010/0076417 | A1 | 3/2010 | Suckewer et al. |
| 2011/0098790 | A1 | 4/2011 | Daxer |
| 2011/0319876 | A1 | 12/2011 | Feingold |
| 2012/0040397 | A1 | 2/2012 | Luo et al. |
| 2012/0238904 | A1 | 9/2012 | Manns et al. |
| 2012/0267510 | A1 | 10/2012 | Gross et al. |
| 2013/0053952 | A1 | 2/2013 | Jun et al. |
| 2014/0012240 | A1 | 1/2014 | Ho et al. |
| 2015/0290030 | A1 | 10/2015 | Suckewer et al. |

FOREIGN PATENT DOCUMENTS

| | | | |
|---|---|---|---|
| WO | WO 2008/055118 | 5/2008 | |
| WO | WO 2011/029095 | 3/2011 | |
| WO | WO-2011029095 A2 * | 3/2011 | ......... A61F 9/00834 |
| WO | WO 2014/198406 | 12/2014 | |
| WO | WO 2017/210374 | 12/2017 | |

OTHER PUBLICATIONS

International Preliminary Report on Patentability in International Application No. PCT/US2016/037277, dated Dec. 12, 2017, 12 pages.
International Preliminary Report on Patentability in International Application No. PCT/US2017/035333, dated Dec. 13, 2018.
International Search Report and Written Opinion in International Application No. PCT/US2017/035333, dated Aug. 3, 2017.
International Search Report and Written Opinion dated Oct. 4, 2016 in international application No. PCT/US2016/037277, 14 pgs.
Olsen, "On the calculation of po,ver from curvature of the cornea," British Journal of Ophthalmology, 70, 152-154 (1986).
Winkler "Nonlinear optical macroscopic assessment of 3-D corneal collagen organization and axial biomechanics," I OVS, vol. 52, 8818-8827, 2011.
Binder, "Intracorneal inlays for the correction of presbyopia and low hyperopia," Ophthalmology Times, Dec. 2015, retrieved on Mar. 10, 2021, retrieved from URL <https://www.ophthalmologytimes.com/view/intracorneal-inlays-correction-presbyopia-and-low-hyperopia>, 9 pages.
Binder et al., "Intracorneal inlays for the correction of ametropias," Eye & Contact Lens, 2015, 41(4):197-203.

* cited by examiner

APPARATUS FOR CHANGING THE REFRACTIVE POWER OF THE CORNEA

CROSS-REFERENCE TO RELATED APPLICATION

This application is a § 371 National Stage Application of PCT/US2017/035333, filed on May 31, 2017, which claims priority from German Application No. 10 2016 110 005.6, filed on May 31, 2016, which are incorporated herein by reference in their entirety, including FIGS. 1, 2, and 3 as originally filed.

FIELD OF THE INVENTION

The invention relates to an apparatus for changing the refractive power of the cornea, in particular for correcting hyperopia (farsightedness) or presbyopia (age-related farsightedness), by operatively changing the curvature of the cornea. The invention relates in particular to an apparatus exhibiting injection means having at least one hollow needle for injecting an optically transparent filling material having a predetermined refractive index into an intrastromal corneal pocket.

BACKGROUND

The human eye is an optical imaging system having different components responsible for refracting the light. Here its refractive power consists first of all on the combination of light refraction at the cornea and at the lens. The refractive power is measured in diopters (dpt) that corresponds to the inverse of the focal length in meters.

The refractive power of the cornea essentially corresponds to that of a convex-concave lens, the convex outer side of the cornea typically exhibiting a slightly larger radius of curvature (for example 7.7 mm) than the concave inner side (for example 6.8 mm). Taking into account the typical refractive indices for the stromal tissue of the cornea (for example 1.376) and of the intraocular fluid behind the cornea (for example 1.336) and of air (1.0), the refractive power of the cornea can for example be estimated to be approximately 43 dpt. Taking into account the exemplary values that have been mentioned, the convex front (positive lens) has a contribution of approximately 49 dpt and the concave rear (negative lens) a contribution of approximately −6 dpt. In comparison to the eye lens whose refractive power varies between approximately 19 dpt and 34 dpt during accommodation, the cornea proves to be the optical component that is of greater importance for the total refractive power. How to calculate the refractive power of the cornea can for example be gathered from the work by Olsen "On the calculation of power from curvature of the cornea," British Journal of Ophthalmology, 70, 152-154 (1986).

Ametropia is usually due to a defective curvature of the cornea relative to the length of the eyeball. If it is curved too strongly, the refractive power is too high. Light beams that are incident in parallel of a very distant object are then concentrated in front of the retina, therefore the imaging on the retina is out of focus, the eye is myopic (short sighted). If the curvature of the cornea is too weak, the refractive power is too low and the eye is hyperopic (far sighted). When the amplitude of accommodation of the lens decreases with age, age-related farsightedness appears. This can be counteracted using a locally limited change in the curvature of the cornea, which makes the eye bifocal.

LASIK (laser-in-situ-ceratomileusis) is a type of eye surgery for correcting the pre-mentioned types of ametropia, that is now wide-spread. Here the curvature of the cornea is adapted by removing tissue by means of laser ablation. Removing the tissue cannot take place on the surface of the cornea since the epithelial layer that is present there is on the one hand very algesic, on the other hand the change in refraction is reversed by regrowth and healing reactions also lead to turbidity in the corneal stroma. For this reason, at first a thin corneal lamella is cut and the "flap" thus produced is folded open. Then the material removal can take place with a high degree of precision inside the corneal stroma by means of excimer laser ablation. After the tissue removal, the flap is then folded back again and the patient can see clearly. In particular myopia correction, where tissue is removed centrally on the optical axis, can be done very well using the LASIK method up to high degrees of ametropia up to more than 10 dpt.

Hyperopia or presbyopia correction, however, then proves to be markedly more difficult. Making the cornea steeper, i.e. a reduction in the radius of curvature by means of tissue removal, is possible by means of LASIK only as a result of an annular removal of material. Even in the case of low ametropia of a few diopters, the LASIK method shows problems concerning the stability and reproducibility of the correction.

To achieve a higher refractive power of the front eye section, the curvature of the cornea can be modified by fixed, permeable hydrogel lenses that are inserted into intrastromal pocket that has been precut by means of a laser. However, these inlays are only suitable for low corrections of the refractive power, see, e.g., Binder "Intracorneal inlays for the correction of presbyopia and low hyperopia," Ophthalmology Times EUROPE, Dec. 1, 2015.

U.S. Pat. No. 5,964,748 (Peyman) and U.S. Pat. No. 8,409,177 B1 (Lai) propose to insert a liquid implant into the cornea. Also in the case of these works, at first an intrastromal pocket is cut into the cornea, referred to as a corneal pocket below. This can be done using laser light or a surgical scalpel. In particular, for the hyperopia correction, the corneal pocket is situated centrally in front of the lens at right angles to the optical axis, c.f. in particular Peyman FIG. 37 and associated description of the figures. Into the corneal pocket there is then injected a transparent biocompatible fluid that fills the pocket and thereby makes the cornea thicker overall. Bulging can then occur on the corneal front which results in the corneal outside being more steep, i.e. a reduction in the front radius of curvature and thus to an increase in the refractive power.

The optically transparent biocompatible fluid can for example be a gelable collagen, but also a silicone gel or an injectable poly (methyl methacrylate) (PMMA) can be considered. It is further also possible to use hydrogels that contain hyaluronic acid or other transparent compounds that are certified for injection into tissue.

The Lai patent further develops the suggestion by Peyman to that extent that the liquid injected into the corneal pocket should be polymerizable under the influence of light and that a photo curing step after the end of the injection solidifies the liquid implant. As a result, the implant is immobilized in its current position, and the change in the refractive index is stabilized at the same time.

SUMMARY

In one aspect, the disclosure features apparatus for changing the refractive power of the cornea by injecting a transparent filling material, that is able to determine the correct injection amount.

The apparatus for changing the refractive power of the cornea includes injection means having at least one hollow needle for injecting at least one optically transparent filling material having a predetermined refractive index into an intrastromal corneal pocket, characterized by a controllable injection drive that is coupled at least indirectly to the injection means and is designed for changing an amount, to be injected, of the at least one filling material. The apparatus further includes a device for optical coherence tomography (OCT) that is designed for monitoring the area of the corneal pocket by means of measurement of depth profiles of the cornea on a repeatedly cycled-through scan pattern, and a computing unit that is designed and/or configured to determine from the measurement data of the OCT device at least the radius of curvature of the front of the cornea, and optionally the rear of the cornea, keeping pace temporally with the repetitions of the scan pattern cycle during the injection. In this apparatus, the computing unit is designed and/or configured to control the injection drive for changing the injected amount of the at least one filling material, and to be precise on the basis of the radius of curvature of the front of the cornea and, in some embodiments, the rear of the cornea, and/or such until a predetermined target criterion is fulfilled.

In some embodiments, the apparatus is used once a suitably placed corneal pocket has been created in the cornea of the patient by a physician.

In another aspect, the new apparatus is used in methods to continuously measure the cornea during the injection of the filling material into the corneal pocket using an OCT device at least in the area of the pocket and to carry out from these measurement data an automatic evaluation as to the extent with which the target of the injection has been achieved. This evaluation is preferably likewise used automatically to control the injection means for changing the injected amount of the filling material if the target has not yet been reached, and automatically to search for the optimum filling amount for the therapeutic target. The apparatus is preferably designed and/or configured as an autonomous apparatus.

The apparatus and methods offer the technical effect that the correct injection amount can be determined automatically from OCT measurement data during the filling of the corneal pocket based on the fulfillment of a target criterion for optical attributes, to be achieved, of the cornea. For this purpose, the apparatus can be correspondingly designed and/or configured.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

The invention is explained in more detail below using figures.

DETAILED DESCRIPTION

The inventors of the present description have carried out experiments on enucleated pigs eyes so as to investigate more closely the feasibility of producing a corneal pocket by means of laser light and the subsequent bulging of the cornea by liquid injection. Among others it was found that the liquid volume in the corneal pocket readily assumes the shape of a lenticule. The investigation concentrated on the achievable results for the extent and predictability of the change in refractive power.

The deformation of the cornea relative to the change of the radius of curvature at the front surface and the lenticule shape of the injected filling material are strongly dependent on the elastic-plastic properties of the cornea, and also on the size of the pocket. Here the mechanical properties of the corneal stroma vary by a factor of up to 3 from one person to another, see e.g. Winkler "Nonlinear optical macroscopic assessment of 3-D corneal collagen organization and axial biomechanics," IOVS, Vol. 52, 8818-8827, 2011.

In the experiments, changes in refractive power by up to 9 dpt could be realized, thus very much favoring the further development of the methodology, since other methods at present do not make possible such big increases in the refractive power.

Figure 1:
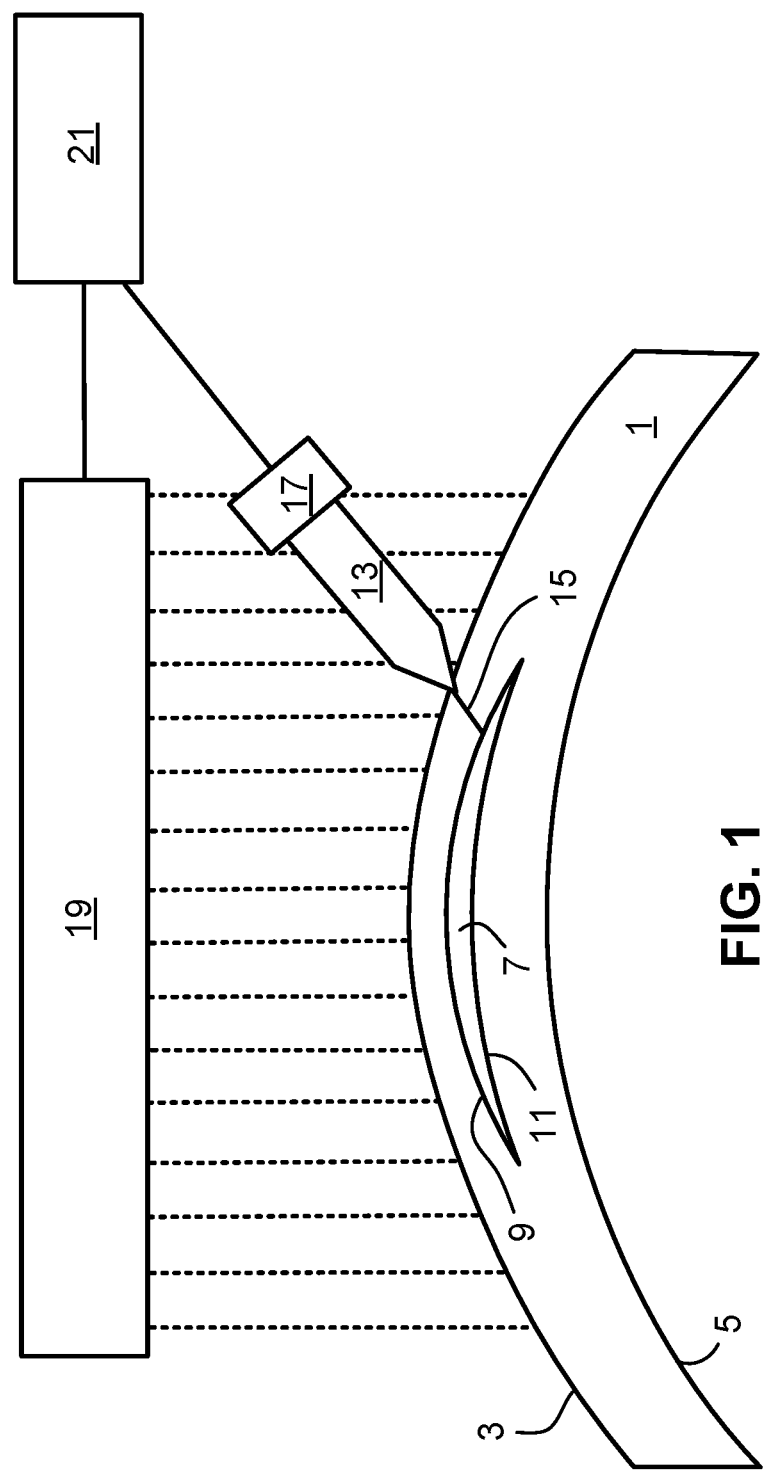
FIG. 1 shows a sketch of the apparatus for changing the refractive power of the cornea.

From FIG. 1 a schematic sketch of the inventive apparatus can be gathered. It exhibits an OCT device (19) that detects, prior and in particular during the injection, by interferometric evaluation of back scattered measurement light, depth profiles of the cornea (1) at least in the area of the corneal pocket (7) and transmits the measurement data either directly or in processed form, e.g., as sections of the cornea (1), to the computing unit (21). The measurement of an individual depth profile is also termed an A-scan and takes place as a punctual measurement. To estimate a.o. the curvature of the corneal front (3) and of the rear (5), a multiplicity of A-scans takes place at different points of the cornea (1) that are predetermined in view of the position and size of the corneal pocket (7). The totality of the measurement points forms the scan pattern. The vertical, dotted lines in FIG. 1 indicates the individual OCT A-scans along the extent of the cornea. If the scan pattern is cycled through once, i.e. one depth profile each is detected for each point of the scan pattern, then from all the measurement data it is possible to draw conclusions as to the shape of the cornea (1) and possibly the corneal pocket (7). The scan pattern can be one or two dimensional, i.e. the measurement points can be situated on a line grid or also on a two dimensional grid. The distances of the grid points can vary in this case.

In the simplest case, the grid points of a one dimensional grid are cycled through as scan pattern of the OCT device (19) along a line at right angles to the optical axis across the center of the corneal pocket—this is also termed a B-scan. The OCT device (19) carries out a measurement of the scattering intensity of the cornea (1) for each grid point of the line, so that the data set of this scan pattern provides a section of the cornea (1) that is in that plane that is generated by the line of the scan pattern and by the optical axis (drawing plane of FIG. 1). From an OCT section, at least the radius of curvature of the front (3) of the cornea, and in some embodiments of the rear (5) of the cornea (1), can be determined.

For continuously observing the cornea (1) in the area of the corneal pocket (7), the scan pattern has to be cycled through in a temporarily repetitive form in order to detect changes during the injection of the filling material.

The determination at least of the radius of curvature of the front (3) of the cornea and optionally the rear (5) of the cornea (1) is to be carried out by the computing unit (21) keeping pace temporally with the repetitions of the cycles of the scan pattern. In this manner, at, with or after each cycle or at least one scan pattern cycle, a renewed determination at least of the radius of curvature of the front (3) of the cornea, and in some embodiments of the rear (5) of the cornea can take place. Thus, it can be envisaged that this does not necessarily mean that a determination of the radius of curvature has to take place for each single scan pattern cycle, but it is also possible to initially cycle through and evaluate several subsequent scan patterns, it being possible to predetermine a corresponding number of the cycles, before a further determination takes place. A single scan pattern cycle usually requires only a few milliseconds, so that in the case of slow injection of the filling material it can happen that a change in the radius or radii of curvature only results across a plurality of cycles of the scan pattern.

Since the injection of the filling material effects a bulge of the corneal front (3), the radius of curvature of the front (3) and potentially also the back of the cornea (1) provides insight as to the increased refractive power. The radii of curvature that have been determined can therefore serve as a basis to control the injection drive (17) by means of the computing unit.

Since the inventive apparatus is preferably designed for the autonomous control of the injection, in particular of the injection speed, the computing unit (21) can advantageously also be designed and/or configured to decide and/or to determine autonomously which number of cycles of the scan pattern it analyses before it carries out the next check of the target criterion and decides as to the further progress of the injection.

In a preferred case, the predetermined target criterion of the therapeutic success is reaching a predetermined desired value for the refractive power of the cornea (1). Since the injection of the filling material effects a bulging of the cornea, the refractive power is a strictly monotonously increasing function of the injected amount of filling material. Under the assumption that the corneal pocket (7) was produced in a suitable depth and size, the target criterion can then be complied with by the precise coincidence of measured and calculated refractive power with the predetermined desired value.

When the transparent filling material exhibits at least essentially the same index of refraction as the stromal tissue of the eye, the refractive power of the cornea (1) having the filled corneal pocket (7) can be calculated as that of a convex-concave lens only using the radii of curvature determined from the OCT section. Else the travel of the corneal pocket (7) along the optical axis and the radii of curvature of the front (9) and the rear limiting face (11) of the corneal pocket (7) have to be additionally determined from the OCT section. Here the travel is the largest distance that can be determined between the front (9) and the rear (11) of the filled corneal pocket (7). Using these additional measurement values, the refractive power of the cornea can be calculated taking into account the indices of refraction of the filling material and the stromal tissue as the refractive power of a concentric arrangement of a plurality of lenses.

The concentric arrangement of a plurality of lenses can here be considered as a convex-concave lens having embedded therein a lens that is formed by the filled corneal pocket (7). The shape of the embedded lens is typically that of a convex-concave lenticule; in the case of large amounts of filling material or in the case of small pockets—in particular for presbyopia correction—it can also assume a biconvex shape.

The inventive apparatus comprises a computing unit (21) that can for example be a personal computer (PC) and that—for example by appropriate software—is designed and/or configured to carry out the mentioned computations from the electronic measurement-data sets of the OCT device (19). At least the hardware of a corresponding OCT device (19) is available commercially. The OCT device (19) and the computing unit (21) can form a constructional unit.

The inventive apparatus comprises injection means (13, 15) having at least one hollow needle (cannula) (15). The at least one hollow needle (15) is connected to a reservoir (13) for at least one transparent filling material either directly or by means of a flexible tube. As a rule, the filling amount of the reservoir (13) is predetermined. The reservoir (13) can be formed by a flexible container or also by a fixed container having a piston (not illustrated) that can be pushed into the reservoir (13). In a preferred design, pressure is exerted in a controlled manner on the filling material so that it can—possibly conveyed by a flexible tube and—exit the end of the hollow needle (15). Here the pressure can be exerted either on the flexible walls of the reservoir (13) or on the piston in the manner of a conventional syringe.

The injection means (13, 15) can also comprise a plurality of hollow needles (15) that enable the simultaneous injection of the filling material at different access points for the corneal pocket (7) in the eye of the patient. The injection means (13, 15) can further comprise a plurality of reservoirs (13), it being possible to assign each reservoir (13) to at least one predetermined hollow needle (15). The individual reservoirs (13) can contain different substances as transparent filling materials that a.o. differ in terms of their index of refraction. Assigning the reservoir (13) to the hollow needles (15) can be changed—for example by closing and opening valves.

Simply for the purpose of simplifying the description it is assumed below that the injection means (13, 15) comprise precisely one reservoir (13) having precisely one filling material and precisely one hollow needle (15).

The inventive apparatus further exhibits an injection drive (17) that is preferably designed to exert a controlled pressure on the liquid in the reservoir (13) on the basis of electric control signals from a control unit. The injection drive (17) preferably comprises an electric motor. The control unit can be integrated in terms of construction into the injection drive (17) and receive digital commands of the computing unit (21) and translate them into electric control signals, e.g. analog voltage values. As an alternative, the computing unit (21) itself can output electric control signals for driving the injection drive (17) by means of a converter interface.

The injection drive (17) can for example be constructed from two parallel plates with distance relative to each other can be set by a controllable electric motor. A flexible bag having a liquid filling material can be arranged between the plates such that the liquid is pressurized when the plates approach each other and exits the hollow needle (15)—possibly via a flexible tube. In this way, there can be formed between the injection drive (17) and the injection means (13, 15) a preferably mechanic coupling that permits a change in the amount of the filling material to be injected by driving the injection drive (17). A coupling between the injection drive (17) and the injection means (13, 15) can basically also be formed in a different way to produce at least one indirect coupling that ensures a controlled change in the amount of filling material to be injected. It is regarded as advantageous to design the reservoir (13) in the manner of a syringe and to provide the injection drive (17) as an electric motor that controls the position of the piston. In this manner, driving the injection drive (17) can generate both a positive pressure and a negative pressure in the reservoir (13) relative to the end of the hollow needle (15). The injection drive can thereby be controlled to vacuum off again from the corneal pocket (7) any excessively injected filling material.

The amount of filling material to be injected as a whole into the eye of the patient is in the volume order of magnitude of microliters or cubic millimeters. The injection drive (17) should have a sufficient positioning accuracy so as to change the injection volume in small steps, preferably by about 0.1 microliters per step.

The apparatus described up to now comprising injections means (13, 15), an injection drive (17), an OCT device (19), and a computing unit (21), is in a position to automatically fill the pocket (7) with a transparent filling material for the intended increase in refractive power of a far-sighted eye into which previously a radially-symmetric central corneal pocket (7) was created. Here it is precisely that amount of filling material that is injected that produces the predetermined desired value of the refractive power. Although the a priori unknown mechanical attributes of the corneal stroma of the patient are not determined explicitly, but they are utilized as appropriate, because they are taken into account implicitly in the effect measurement.

Figure 2:
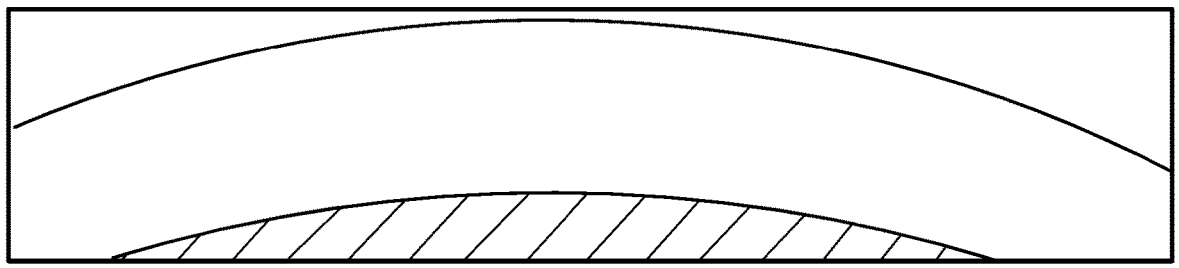
FIG. 2 shows an OCT section of the cornea of an enucleated pigs eye determined from a line grid as scan pattern.
Figure 2:
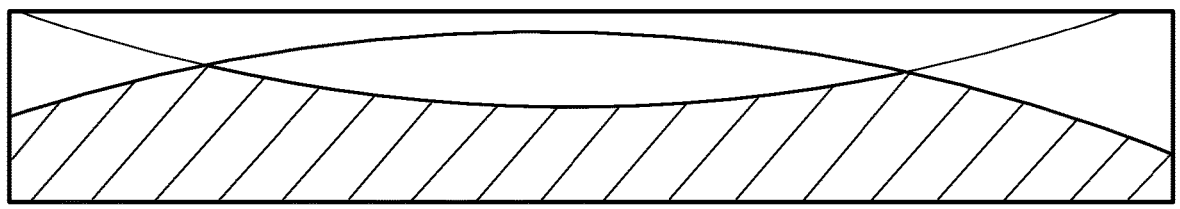

From FIG. 2 it can be gathered what a section of the cornea (1) determined by the OCT device (19) looks like for a line grid as scan pattern. In the upper part of the image, a cross section through the entire cornea (1) of an enucleated pigs eye can be seen with front (3) and rear (5). The measurement range of the OCT device (19) is additionally limited, typically to a depth interval having a width of approximately 2 mm. However, it can be shifted by changing the reference-arm length. The lower part of the image of FIG. 2 shows a measurement range shifted along the direction of the optical axis of the eye, from which the radius of curvature of the corneal rear (5) can be determined better than from the measurement range of the upper part of the image that in turn shows better the curvature of the front (3). The lower part of the image also contains a mirror-image representation of the front (3), being an artefact of the OCT recording. In principle, both radii of curvature could be determined from the lower part of the image alone, but the contrasts that are weak in the shifted measurement range and originate from the corneal front (3) make automatic image evaluation difficult here. However, it is very well possible to design the OCT device (19) such that it simultaneously works with different reference-arm lengths and at the same time detects measurement ranges that are shifted relative to each other and are even far apart, see, for example, DE 10 2007 023 293 B3.

Figure 3:
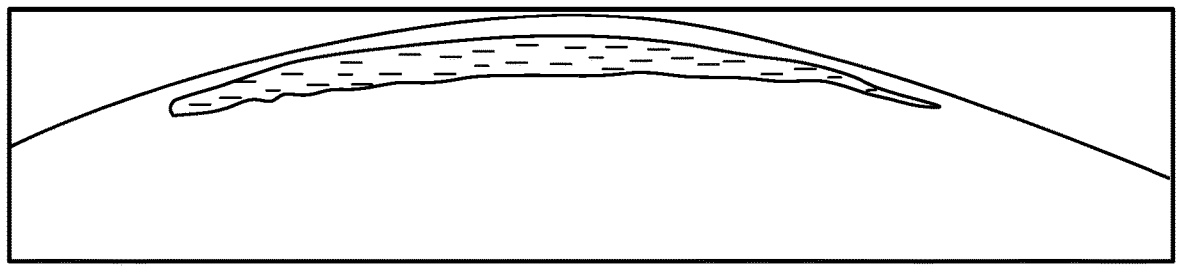
FIG. 3 shows an OCT section of the eye from FIG. 2 after creating and filling a corneal pocket with a viscoelastic hydrogel containing 1% sodium hyaluronate.
Figure 3:
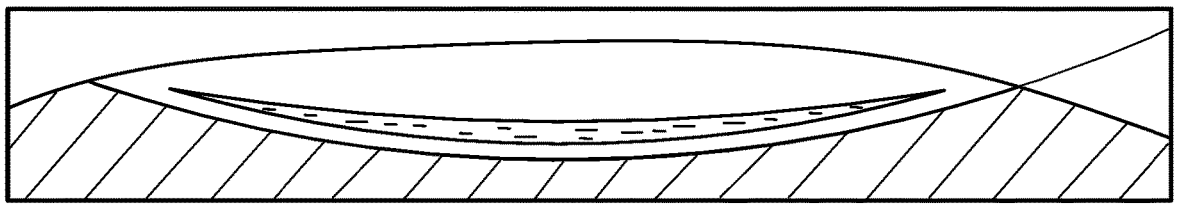

FIG. 3 now shows the same cornea (1) after creating and filling the corneal pocket (7). The bulging of the front (3) can be seen in comparison to FIG. 2. The pocket (7) likewise can be made out very well since in comparison to the stromal tissue the liquid filling material backscatters light only very weakly. The morphology of the pocket (7) corresponds to that of a lenticule as it is being removed during conventional myopia correction by means of LASIK. To that extent in fact a synthetic lenticule is inserted into the natural tissue. However, it can also be seen in FIG. 3 that the lenticule does not necessarily have to establish itself complete radial-symmetrically even when designing a radial-symmetric pocket (7). The reason for this can be assumed to be in the varying mechanical attributes of the cornea (1) in the area of the pocket (7).

If deviations occur between the actual and the originally planned shape of the filled corneal pocket (7) this can introduce an irregular or regular astigmatism. The irregular astigmatism can for example come about as a result of a viscous filling material not yet having spread uniformly in the corneal pocket (7) immediately after the injection and stably filled all pocket edges. The surgeon can intervene by pressing on and/or wiping across the corneal front (3) in a supporting manner so that a state of equilibrium is established as soon as possible.

The regular astigmatism can basically be countered in that the surgeon opens further the corneal pocket (7) at some edge locations so that the shape of the pocket (7) is set differently by redistributing the filling material. Such a reworking can preferably be carried out by laser cutting in the surroundings of the pocket edge even in the case of a pocket (7) that has already been filled.

To support the surgeon, the inventive apparatus can be designed such that it detects and quantifies the presence of a regular astigmatism and even shows at which edge points the pocket (7) should be opened further to correct the astigmatism.

To this end it is at first necessary that the OCT device (19) repeatedly cycles through the grid points of a two-dimensional grid in the plane at right angles to the optical axis as a scan pattern in the area of the corneal pocket (7). For example a two-dimensional scan pattern can comprise the intersection points of intersecting line groups or also the nodes of a honeycomb grid. It is advantageous when here a measurement point of the scan pattern is on the optical axis where the greatest thickness of the corneal pocket (7) is to be expected.

The computing unit (21) of the apparatus is furthermore designed and/or configured to calculate from the measurement data of the OCT device (19) keeping pace temporally with the repetitions of the cycles of the two-dimensional scan pattern, a three-dimensional (3D) model of the shape of the cornea (1) and of the corneal pocket (7) filled with the filling material. On account of the rather simple structure of the target shapes, this is possible without any problems by means of an interpolation of the relative distances determined by means of OCT on the discrete grid points of the scan pattern.

The determined 3D-model represents a compound optical system having known indices of refraction. The light-guiding attributes of such a system can nowadays be simulated effectively, in particular by applying modern software for raytracing. On top of this, graphic boards of today's PCs are particularly designed for such computing operations. The computing unit (21) of the inventive apparatus can therefore be designed to determine, keeping pace temporally with the model computation, the regular astigmatism of the optical system formed by the cornea (1) and the filled corneal pocket (7) and to represent it as a tuple of parameters.

For example, the computing unit (21) can compute for a multiplicity of directions at right angles to the optical axis, the focusing of a simulated, collimated light beam during the beam passage through the optical system according to the 3D model and thus determine those two directions that exhibit the largest and the smallest refractive power. They can be referred to as astigmatic main axes. The main-axes directions—described as plane directional vectors—and the computed refractive powers assigned to these main axes, then together form a tuple of parameters that describes the astigmatism.

The computing unit (21) constantly repeats the calculation of the 3D model and the evaluation of the astigmatism during the injection and during the course establishes a temporally variable actual-value tuple. This can be compared to a desired-value tuple as target.

The desired-value tuple can for example be predetermined such that it only provides for a predetermined refractive power and no astigmatism. In the case of the example above, where two main-axes directions and two refractive powers are determined as actual-value tuples, in the desired-value tuple then both refractive powers where equal to the predetermined value and the main-axes directions were arbitrary, random or zero.

However, the desired-value tuple can target a predetermined astigmatism of the cornea (1) for example to correct an astigmatism present in the lens.

In each case it can be expected that it will not be readily possible to make the actual-value tuple coincide with the desired-value tuple since the only control parameter that is available is the filling amount of the corneal pocket (7). In particular it can fail to precisely set two different refractive powers along differing main-axes directions at the same time only by means of the filling amount.

The target criterion should therefore be the assumption of an optimum that can be described by a minimum "distance" of actual-value tuple and desired-value tuple that the computing unit (21) is to find. The distance can here be understood to mean generally a positive value attribution in the sense of a norm to the pair of actual-value tuple and desired-value tuple. The distance is zero if both coincide and otherwise greater than zero. A precise definition of the distance can only be carried out in view of the specific application and by predetermining the parameters that arise in the tuples. The distance is ultimately nothing else than an appropriately selected mathematicly function of actual-value tuple and desired-value tuple. As such it can be easily coded in software, and the computing unit (21) is then designed and/or configured to check the approximation of the actual-value tuple toward a predetermined desired-value tuple in terms of a minimum distance as target criterion.

It is preferably provided that the computing unit (21) controls the injection drive (17) so that a minimum distance of the actual-value tuple from the desired-value tuple arises, preferably to comply with the target criterion. While the computing unit (21) controls the injection drive (17) so as to determine the minimum distance of actual-value tuple and desired-value tuple and thus to comply with the target criterion, a short-term running past the looked-for optimum is to be expected. It is therefore particularly advantageous if the injection drive (17) is designed and/or able both to increase and also to reduce the filling amount in the corneal pocket (7).

When the actual-value tuple that is found finely complies with the target criterion and exhibits the minimum distance from the desired-value tuple, as a rule this distance is not zero. The computing unit (21) can now also be designed and/or configured to calculate from the actual-value tuple, when the target criterion is complied with, and from the predetermined desired-value tuple and/or to output at which edge points the corneal pocket (7) is to be enlarged in order to further reduce the remaining distance between actual-value tuple and desired-value tuple.

To achieve this, the mechanical attributes of the stromal tissue can be modelled at least in the edge regions of the pocket (7). To this end, the computing unit (21) can be designed and/or configured. Modelling now presupposes that shape variations of the corneal pocket (7) can be ascribed solely to the mechanical attributes of the stromal tissue and are not determined by the course of the injection procedure. This requirement should be approximately fulfilled when the treating surgeon after the injection awaits the equal distribution of the filling material in the pocket or induces it by supporting exertion of pressure.

The actual shape of the filled corneal pocket (7) is known to the computing unit (21), and this shape for example in FIG. 3 shows a.o. areas of varying thickness along the lenticule edge. From this it can be deduced that some areas of the tissue are more easily pressed apart by the filling material than others, and it can be assumed that this mechanical behavior changes only slowly in the local environment. If therefore a rather thick edge area of the pocket (7) is opened up further, it can be expected that also the tissue of the enlarged edge can be easily pressed apart by the filling material.

Using this mechanical information indirectly coded in the pocket shape, it is now possible to enter into a numerical modelling e.g. using a finite element method, to model the change in shape, that is to be expected, of the pocket volume, if edge regions of the pocket (7) are further opened up using the laser. These pocket shapes changed in the numerical modelling—i.e. simulated—are again becoming the subject of a raytracing analysis as described further above. From this analysis, those pocket shapes can be predicted that are likely to bring about a better optical result, i.e. a smaller distance between actual-value tuple and desired-value tuple. From the prediction of a more favorable pocket shape it is again possible to determine those edge positions of the pocket (7) actually produced in the eye of the patient that should be opened with priority to achieve the more favorable pocket shape. On the basis of the described model calculations, the computing unit (21) is thus in a position to issue a recommendation to the surgeon, e.g. by outputting vector coordinates relative to the optical axis, where he/she could start the reworking with the greatest likelihood of success.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:
1. A system for changing a refractive power of a cornea, comprising
    an injection system having at least one hollow needle arranged to inject at least one optically transparent filling material having a predetermined refractive index into an intrastromal pocket in the cornea having the refractive power;
    a computing unit;
    a controllable injection drive coupled directly or indirectly to the injection system and to the computing unit, wherein the injection drive is controlled by the com- puting unit to adjust an amount to be injected of the at least one filling material; and
a device for optical coherence tomography (OCT) arranged to monitor an area of the corneal pocket by measuring depth profiles of the cornea to produce measurement data and to transmit the measurement data to the computing unit;
wherein the computing unit is arranged and configured to determine from the measurement data of the OCT device at least a radius of curvature of a front surface of the cornea, and
wherein the computing unit is arranged and configured to control the injection drive to adjust an injected amount of the at least one filling material based on the radius of curvature of the front of the cornea until a predetermined first target criterion is fulfilled.

2. The system of claim 1, further comprising the optically transparent filling material, wherein the predetermined refractive index of the filling material substantially coincides with a refractive index of stromal tissue of the cornea and wherein the computing unit is arranged and configured to compute the refractive power of the cornea as that of a convex-concave lens based on at least the determined radius of curvature of the front surface of the cornea.

3. The system of claim 2, wherein the computing unit is configured to check a coincidence of the computed refractive power of the cornea with a predetermined desired value as a second target criterion.

4. The system of claim 1, wherein the computing unit is arranged and configured to determine from the measurement data of the OCT device a travel of the corneal pocket along an optical axis of the cornea and radii of curvature of front and rear limiting faces of the corneal pocket keeping pace temporally with repetitions of a scan pattern cycle.

5. The system of claim 4, wherein the computing unit is arranged and configured to check a coincidence of the computed refractive power of the cornea with a predetermined desired value as a third target criterion.

6. The system of claim 1, wherein grid points of a two-dimensional grid in a plane at right angles to an optical axis are predetermined as a scan pattern of the OCT device.

7. The system of claim 6, wherein the computing unit is arranged and configured to compute from the measurement data of the OCT device a three-dimensional model of a shape of the cornea and of the corneal pocket filled with the filling material.

8. The system of claim 7, wherein the computing unit is arranged and configured to keep pace temporally with a model computation, to determine astigmatism of an optical system formed by the cornea and the filled corneal pocket and to represent the optical system as a tuple of parameters.

9. The system of claim 8, wherein the computing unit is arranged and configured to check convergence of an actual-value tuple toward a predetermined desired-value tuple in terms of a minimum distance as a third target criterion.

10. The system of claim 9, wherein the computing unit is arranged and configured to compute from the actual-value tuple during fulfillment of the third target criterion and from the predetermined desired-value tuple at which edge positions the corneal pocket is to be opened up further to reduce a remaining distance between the actual-value tuple and the predetermined desired-value tuple.

11. The system of claim 10, wherein the computing unit is arranged and configured to output at which edge positions the corneal pocket is to be opened up further to reduce the remaining distance between the actual-value tuple and the desired-value tuple.

12. The system of claim 1, wherein the system is arranged and configured to correct hyperopia or presbyopia.

13. The system of claim 1, wherein the OCT device is controlled to provide a repeatedly cycled-through scan pattern, and wherein the computing unit is further configured to keep pace temporally with repetitions of the repeatedly cycled-through scan pattern during an injection.

* * * * *